United States Patent [19]

Bech et al.

[11] Patent Number: 5,208,158
[45] Date of Patent: May 4, 1993

[54] OXIDATION STABLE DETERGENT ENZYMES

[75] Inventors: Lene M. Bech, Naestved; Sven Branner, Lyngby; Klaus Breddam, Glostrup; Hanne Groen, Copenhagan, all of Denmark

[73] Assignee: Novo Nordisk A/S, Bagsvaerd, Denmark

[21] Appl. No.: 553,934

[22] Filed: Jul. 17, 1990

[30] Foreign Application Priority Data

Apr. 19, 1990 [DK] Denmark ................ 971/90

[51] Int. Cl.$^5$ .............. C12N 9/50; C12N 9/26; C12N 9/20; C12N 9/42
[52] U.S. Cl. .............................. 435/219; 435/198; 435/209; 435/183; 435/188; 435/201
[58] Field of Search ............. 435/219, 201, 198, 209, 435/183, 188

[56] References Cited

U.S. PATENT DOCUMENTS

| | | | |
|---|---|---|---|
| 4,467,036 | 8/1984 | Schnepf et al. | 435/320.1 |
| 4,581,352 | 4/1986 | Foster et al. | 514/202 |
| 4,874,696 | 10/1989 | Payne et al. | 435/190 |

FOREIGN PATENT DOCUMENTS

89/06279  7/1989  PCT Int'l Appl. ........... 435/219

OTHER PUBLICATIONS

Skaked et al., Rates of Thiol-Disulfide Interchange . . . Biochemistry, vol. 19, No. 18, pp. 4156–4166, 1980.
Estell et al., *Engineering an Enzyme by Site-directed . . .* , *J. of Biol. Chem.*, vol. 260, No. 11, pp. 6518–6521, 1985.
Stauffer et al., vol. 24, No. 19, pp. 5333–5338, 1969.
Bech et al., Carlsberg Res. Commun., vol. 53, pp. 381–393 (1988).

*Primary Examiner*—David M. Naff
*Assistant Examiner*—Michael V. Meller
*Attorney, Agent, or Firm*—Steve T. Zelson; Elias J. Lambiris

[57] ABSTRACT

Novel chemically modified detergent enzymes are provided, wherein one or more methionines have been mutated into cysteines, said cysteines subsequently being chemically modified in order to confer the enzyme improved stability towards oxidative agents. A novel process for stabilizing detergent enzymes against oxidation is also provided. Furthermore, there are provided detergent compositions comprising these novel oxidation stable detergent enzymes.

12 Claims, 4 Drawing Sheets

OXIDATION STABLE DETERGENT ENZYMES

TECHNICAL FIELD

This invention is within the field of oxidation stable detergent enzymes. More specifically, the present invention relates to novel chemically modified detergent enzymes wherein one or more methionines have been mutated into cysteines, said cysteines subsequently being chemically modified in order to confer the enzyme improved stability towards oxidative agents. The present invention is also directed towards a novel process for stabilizing detergent enzymes against oxidation. Further, the present invention is directed towards a detergent composition comprising these novel oxidation stable detergent enzymes.

BACKGROUND ART

The problems related to a generally low oxidation stability is a well known major obstacle in respect to the activity of detergent enzymes. Due to the presence of bleach active ingredients, the detergent enzymes have to perform their enzymatic action in an oxidative environment, with a consequent loss of activity.

Various solutions have been proposed to the problem, but hitherto oxidation stable detergent enzymes have not been available.

The currently used detergent enzymes have been found by isolating the enzymes from nature and testing them in detergent formulations. Some detergent enzymes have been artificially modified by deletions or substitutions of amino acids within their molecule, in order to achieve novel detergent enzymes with altered chemical and enzymatic properties. Techniques as random and site-directed mutagenesis have been applied from knowledge of the physical and chemical properties of the enzymes, and accordingly these techniques have mostly been applied to proteases.

Especially site-directed mutagenesis of the subtilisin genes has attracted much attention, and various mutations are described in patent publications (see e.g. EP 130,756; EP 214,435; EP 303,761; EP 260,105; WO 87/04461; WO87/05050).

A subtilisin is a serine protease produced by Gram-positive bacteria or fungi. A wide variety of subtilisins have been identified, and in several cases the amino acid sequence has been determined (WO 89/06279 and WO 91/00345). In position 222 these wildtype subtilisins hold a methionyl residue, and this methionyl residue is identified as being responsible for the lability of the enzyme towards oxidative agents (J. Biol. Chem., 244, 5333-5338 (1969)).

Substitution of the residue at position 222 with any other of the 19 essential amino acid residues has been carried out, and the mutants obtained were investigated in respect to relative activity (J. Biol. Chem., 260, 6518-6521 (1985)). Only the Cys-mutant displayed a relative activity in magnitude of the wildtype (56%), but similar to the wildtype this Cys-mutant was unstable to oxidative agents, and a "half life" in the order of 12 minutes in 1 M $H_2O_2$ was found (the wildtype-subtilisins do not contain cystein residues). Among the most oxidation stable mutants the Ala-mutant displayed the highest enzymatic activity (11%), and it did not lose its activity even after 15 minutes in 1 M $H_2O_2$.

For scientific use it has been demonstrated that site-directed mutagenesis can be combined with chemical modifications in order to achieve enzyme derivatives with altered properties. Thus, a chemical modification of a cysteinyl residue introduced in the binding site of carboxy-peptidase-Y has proved to give enzyme derivatives that are more effective in deamidations of peptide amides and peptide synthesis, respectively (Bech, L.M. & Breddam, K.; Carlsberg Res. Commun., 53, 389-393 (1988)).

Therefore, it is an object of the present invention to provide novel chemically altered detergent enzymes, exhibiting improved oxidation resistance, and at the same time substantially retaining their proteolytic activity in respect of their wash performance. Further, it is an object of the present invention to establish a novel process for stabilizing detergent enzymes against oxidation.

BRIEF DISCLOSURE OF THE INVENTION

By way of chemical modification of variants of detergent enzymes, the preparation of novel active chemically modified detergent enzymes, with conferred stability towards oxidative agents, has now surprisingly succeeded.

Thus, according to a first aspect, the present invention provides novel oxidation stable chemically modified detergent enzymes, wherein one or more methionines have been mutated into cysteines, and the cysteines are subsequently modified chemically in order to substitute the hydrogen of the HS-group into a group of the general formula $R^1S-$, wherein $R^1$ is $C_{1-6}$-alkyl.

According to a second aspect, the present invention provides a novel process for stabilizing detergent enzymes against oxidation, whereby a variant of the detergent enzyme, wherein, one or more methionines have been mutated into cysteine, are chemically modified by substitution of the hydrogen of the HS-group of the cysteines into a group of the general formula $R^1S-$, wherein $R^1$ is $C_{1-6}$-alkyl, due to reaction with a compound of the general formula $R^1SSO_2R^2$, wherein $R^1$ is $C_{1-6}$-alkyl and $R^2$ is $C_{1-4}$-alkyl, and the reaction is carried out at pH values in the range 5 to 11.

According to a third aspect, the present invention provides a detergent composition comprising one or more of the oxidation stable detergent enzymes, provided in the form of a detergent additive, preferably a non-dusting granulate or a stabilized liquid.

DESCRIPTION OF DRAWINGS

The invention will be explained in more detail in the following with reference to the figures, wherein

FIG. 2a shows a "wild-type" enzyme with a methionine sidechain.

FIG. 2b shows an enzyme variant, wherein a methionine has been mutated into a cysteine (M→C).

FIG. 2c shows chemically modified enzyme variants of the invention.

FIG. 2d shows an oxidated "wild-type" enzyme.

DETAILED DISCLOSURE OF THE INVENTION

Figure 1:
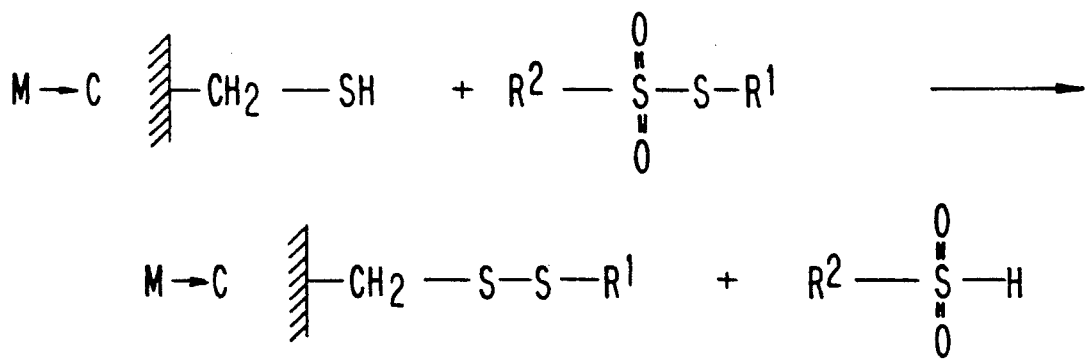
FIG. 1 shows a schematic representation of the chemical modification reaction of the invention in general.
Figure 2A:
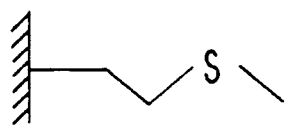
FIGS. 2a-d show a comparison of the structures of various groups attached to the peptide backbone of the detergent enzyme.
Figure 2B:
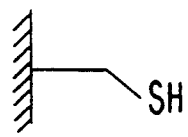
Figure 2C:
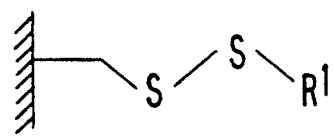
Figure 2D:
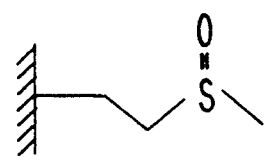

By a chemical modification process according to the present, invention, detergent enzymes, wherein one or more methionines have been mutated into cysteines, are treated with an agent of the general formula $R^1SSO_2R^2$, wherein $R^1$ and $R^2$ are defined below, in order to substitute the hydrogen of the HS-group of the cysteine into a group of the general formula $R^1S$—(cf. FIG. 1). By this process, cysteine is changed into an amino acid that sterically resembles the methionine originally present, but is much more stable towards oxidative agents than methionine (cf. FIG. 2), and an oxidation stable detergent enzyme of the invention is obtained.

Detergent enzymes

In the detergent industry, enzymes have been implemented in washing formulations for more than 20 years. Detergent enzymes comprise amylases, lipases, cellulases and proteases, as well as other enzymes, or mixtures thereof. Commercially most important detergent enzymes are proteases, including subtilisins.

Process for oxidation stabilization

By the process for stabilizing detergent enzymes against oxidation of the invention, a variant of the detergent enzyme, wherein one or been methionines have been mutated into cysteines, are chemically modified by substitution of the HS-group of the cysteines into a group of the general formula $R^1SS$—, wherein $R^1$ is $C_{1-6}$-alkyl, due to reaction with a compound of the general formula $R^1SSO_2R^2$, wherein $R^1$ is $C_{1-6}$-alkyl, and $R^2$ is $C_{1-4}$-alkyl.

Starting compounds

In the process for stabilizing detergent enzymes against oxidation of the invention, starting compounds are variants of detergent enzymes, wherein one or more methionines have been mutated into cysteines.

The starting compounds can be obtained using e.g. site-directed mutagenesis. Cloning procedures and in vitro mutagenesis can be carried out essentially as described in the International Publication, WO 89/06279 (co-pending U.S. patent application Ser. No. 07/294,241)

Preferred starting compounds are amylases, lipases, cellulases or proteases. More preferred starting compounds are subtilisins.

A survey of the amino acid sequence of various subtilisin proteases is given in International Patent Publication No. WO 91/00345. None of these subtilisins carry a cysteinyl residue, whereas they do carry one or more methionyl residues. Thus, in position 222, and adjacent to the active serine, subtilisin proteases hold a methionyl residue, and as previously mentioned, this residue has been identified as being responsible for the lability of the enzyme towards oxidative agents. For comparison, selected partial amino acid sequences for various subtilisin proteases are listed in Table 1. For the sake of clarity, only the residues in the region around the active serine are listed.

TABLE 1

| | COMPARISON OF AMINO ACID SEQUENCE FOR VARIOUS SUBTILISIN PROTEASES | |
|---|---|---|
| No: | 210 | 220 |
| a) | P—G—V—S—I—Q—S—T—L—P—G—N—*—K—*—Y—G—A—Y—N—G—T—S—M—A—S—P—H— | |
| b) | P—G—V—S—I—Q—S—T—L—P—G—G—*—T—*—Y—G—A—Y—N—G—T—S—M—A—T—P—H— | |
| c) | P—G—V—S—I—Q—S—T—L—P—G—G—*—T—*—Y—G—A—Y—N—G—T—S—M—A—T—P—H— | |
| d) | P—G—V—S—I—Q—S—T—L—P—G—G—*—T—*—Y—G—A—Y—N—G—T—S—M—A—T—P—H— | |
| e) | P—G—V—S—V—Y—S—T—Y—P—S—N—*—T—*—Y—T—S—L—N—G—T—S—M—A—S—P—H— | |
| f) | P—G—A—G—V—Y—S—T—Y—P—T—N—*—T—*—Y—A—T—L—N—G—T—S—M—A—S—P—H— | |
| g) | P—G—A—G—V—Y—S—T—Y—P—T—S—*—T—*—Y—A—T—L—N—G—T—S—M—A—S—P—H— | |
| h) | P—G—V—N—V—Q—S—T—Y—P—G—S—*—T—*—Y—A—S—L—N—G—T—S—M—A—T—P—H— | |
| i) | P—G—V—N—V—N—S—T—Y—T—G—N—*—R—*—Y—V—S—L—S—G—T—S—M—A—T—P—H— | |
| j) | P—G—S—W—I—Y—S—T—Y—P—T—S—*—T—*—Y—A—S—L—S—G—T—S—M—A—T—P—H— | |
| k) | P—G—T—S—I—L—S—T—W—I—G—G—*—S—*—T—R—S—I—S—G—T—S—M—A—T—P—H— | |
| l) | P—G—A—S—I—P—S—A—A—W—Y—T—S—D—T—A—T—Q—T—L—N—G—T—S—M—A—T—P—H— | |
| m) | P—G—V—N—V—Q—S—T—Y—P—G—S—*—T—*—Y—A—S—L—N—G—T—S—M—A—T—P—H— | |
| n) | P—G—T—D—I—K—S—T—W—N—D—G—R—T—K—I—I—S—*—*—G—T—S—M—A—S—P—H— | |
| o) | P—G—T—D—I—L—S—T—W—I—G—G—S—T—R—S—I—S—*—*—G—T—S—M—A—T—P—H— | | a = subtilisin BPN' (Wells et al, 1983, Nucleic Acids, Res., Vol. 11, pp. 7911-25)
b = subtilisin amylosaccharificus (Kurihara et al, 1972, J. Biol. Chem., Vol. 247, pp. 5629-31)
c = subtilisin 168 Stahl and Ferrari, 1984, J. Bacteriol., Vol. 159, pp. 811-19)
d = subtilisin mesentericopeptidase (Svendsen et al, 1986, FEBS Let., Vol. 196, pp. 228-32)
e = subtilisin DY (Nedkov et al, 1985, Biol. Chem. Hoppe-Seyler, Vol. 366, pp. 421-30)
f = subtilisin Carlsberg (Smith et al, 1968, J. Biol. Chem., Vol. 243, No. 9, pp. 2184-91)
g = subtilisin Carlsberg (Jacobs et al, 1985, Nucl. Acids Res., Vol. 13, pp. 8913-26)
h = subtilisin 309 (International Patent Publication No. WO 89/06279)
i = subtilisin 147 (Publication No. WO 89/06279)
j = thermitase (Meloun et al, 1985, FEBS Lett. Vol. 183, pp. 195-200)
k = proteinase K (Betzel et al, 1988, Eur. J. Biochem. 178: 155 ff), and Gunkel et al, 1989, Eur. J. Biochem. 179: 185 ff)
l = aqualysin (Kwon et al, 1988, Eur. J. Biochem. 173: 491 ff)
m = Bacillus PB92 protease (European Patent Publication No. 0 283 075)
n = Protease TW7 (Tritirachium album) (International Patent Publication No. WO 88/07581)
o = Protease TW3 (Tritirachium album) (International Patent Publication No. WO 88/07581)
* = assigned deletion Among the subtilisin variants, wherein M222 has been substituted with cystein, those preferred are subtilisin-309-M222C, subtilisin-147-M222C, subtilisin-BPN'-M222C, subtilisin Carlsberg-M222C and proteinase K-M222C. Most preferred is subtilisin-309-M222C.

Chemical modification

Modifying chemical reagents of the general formula $R^1SSO_2R^2$ are commercially available, or can be prepared by traditional organic chemical methods (see "materials and methods").

For sterical reasons, the substituents $R^1$ and $R^2$ have to be of limited size. Therefore, preferred $R^1$-substituents are $C_{1-6}$-alkyl, and most preferred are methyl, ethyl or propyl/isopropyl. Preferred $R^2$-substituents are $C_{1-4}$-alkyl, and most preferred are methyl or ethyl.

Preferred reagents of the general formula $R^1SSO_2R^2$ are methane-methyl-thiosulphonate (MMTS), ethane-methyl-thiosulphonate (EMTS) and propane-methyl-thiosulphonate (PMTS) (see "materials and methods").

The pH should be in the range 5 to 11, and most preferred in the range 8 to 10.

through reaction with $R^1SSO_2R^2$, is designated subtilisin-309-M222C-SR$^1$. If the reagent is MMTS, the notation will be subtilisin-309-M222C-SM. If the reagent is EMTS, the notation will be subtilisin-309-M222C-SE. If the reagant is PMTS, the notation will be subtilisin-309-M222C-SP, and so forth.

According to the invention, any detergent enzyme can be modified chemically in order to achieve an improved oxidation stability. Preferred oxidation stable chemically modified detergent enzymes according to the invention are subtilisin-309-M222C-SM and subtilisin-309-M222C-SP.

Comparative results from the example are shown in the following Table 2.

TABLE 2

Properties of subtilisin-309 variants

| Enzyme | $K_M(mM)$ | $k_{cat}(s^{-1})$ | $k_{cat}/K_M(S^{-1}mM^{-1})$ | rel. activity* | $t_{\frac{1}{2}}(min.)$ | rel. activity** |
|---|---|---|---|---|---|---|
| Subtilisin-309 (wild type) | 1.76 ± 0.06 | 91.2 ± 1.0 | 52 | 100% | 60 | 100% |
| Subtilisin-309 in oxidated state | 2.36 ± 0.09 | 6.10 ± 0.07 | 2.6 | 5% | — | — |
| Subtilisin-309-M222C | 1.82 ± 0.14 | 43.2 ± 0.03 | 23.8 | 46% | 15 | 39% |
| Subtilisin-309-M222C-SM | 2.02 ± 0.08 | 59.0 ± 0.8 | 29 | 56% | >500 | 89% |
| Subtilisin-309-M222C-SP | 2.22 ± 0.12 | 15.7 ± 0.4 | 7.1 | 14% | >500 | — |

*Substrate: Suc—Ala—Ala—Pro—Phe—pNA
**Substrate: DMC (Dimethyl-casein)
— = not measured Products The novel oxidation stable chemically modified detergent enzymes of the invention are detergent enzymes, wherein one or more methionines have been mutated, into cysteines, followed by chemically modification of the cysteines, in order to substitute the hydrogen of the HS-group into a group of the general formula $R^1S—$, wherein $R^1$ is $C_{1-6}$-alkyl.

Preferred oxidation stable detergent enzymes of the invention are amylases, lipases, cellulases or proteases wherein one or more methionines have been mutated into cysteines in order to substitute the hydrogen of the HS-group into a group of the general formula $R^1 S—$, wherein $R^1$ is $C_{1-6}$-alkyl.

More preferred oxidation stable detergent enzymes of the invention are subtilisins.

Most preferred oxidation stable detergent enzymes of the invention are amylases, lipases, cellulases or proteases, wherein one or more methionines have been mutated into cysteines in order to substitute the hydrogen of the HS-group into a group of the general formula $R^1S—$, wherein $R^1$ is $C_{1-3}$-alkyl.

In another embodiment of the invention, preferred oxidation stable detergent enzymes are chemically modified subtilisins, wherein the methionine in position 222, adjacent to the active serine, has been mutated into cysteine, followed by chemical modification, in order to substitute the hydrogen of the HS-group of the cysteines into a group of the general formula $R^1S—$, wherein $R^1$ is $C_{1-6}$-alkyl.

More preferred are oxidation stable chemically modified subtilisins, where the subtilisins are subtilisin-309, subtilisin-147, subtilisin BPN', subtilisin Carlsberg or proteinase K.

Most preferred is a oxidation stable chemically modified subtilisin, which is subtilisin-309.

In the context of this application, a specific notation for the chemically modified detergent enzymes of the invention is used. According to that notation, the M222C variant of subtilisin-309 (subtilisin-309-M222C), which subsequently has be chemically modified As appears from the table, $K_M$ is nearly constant for all enzymes, whereas $k_{cat}$ varies considerably. The "wild type" enzyme possesses the highest specific activity, but evidently, the subtilisin-309-M222C-SM enzyme possesses the best stability towards oxidative environments along with relatively high enzymatic activity.

The non-modified subtilisin-309-M222C variant possesses poor enzymatic activity as well as poor stability.

Detergent compositions

The detergent composition of the invention may comprise a surfactant, which may be of an anionic, non-ionic, cationic or zwitterionic type, or a mixture of these.

The detergent composition of the invention may also contain other detergent ingredients known in the art, such as builders, bleaching agents, bleach activators, anti-corrosion agents, sequestering agents, anti-soil redeposition agents, perfumes, stabilizers for the enzymes and bleaching agents, etc.

The detergent compositions of the invention can be formulated in any convenient form, such as powders, liquids, etc.

The enzymes of the invention may be included in a detergent composition of the invention by adding separate additives containing the detergent enzymes, or by adding a combined additive comprising different detergent enzymes.

Figure 3:
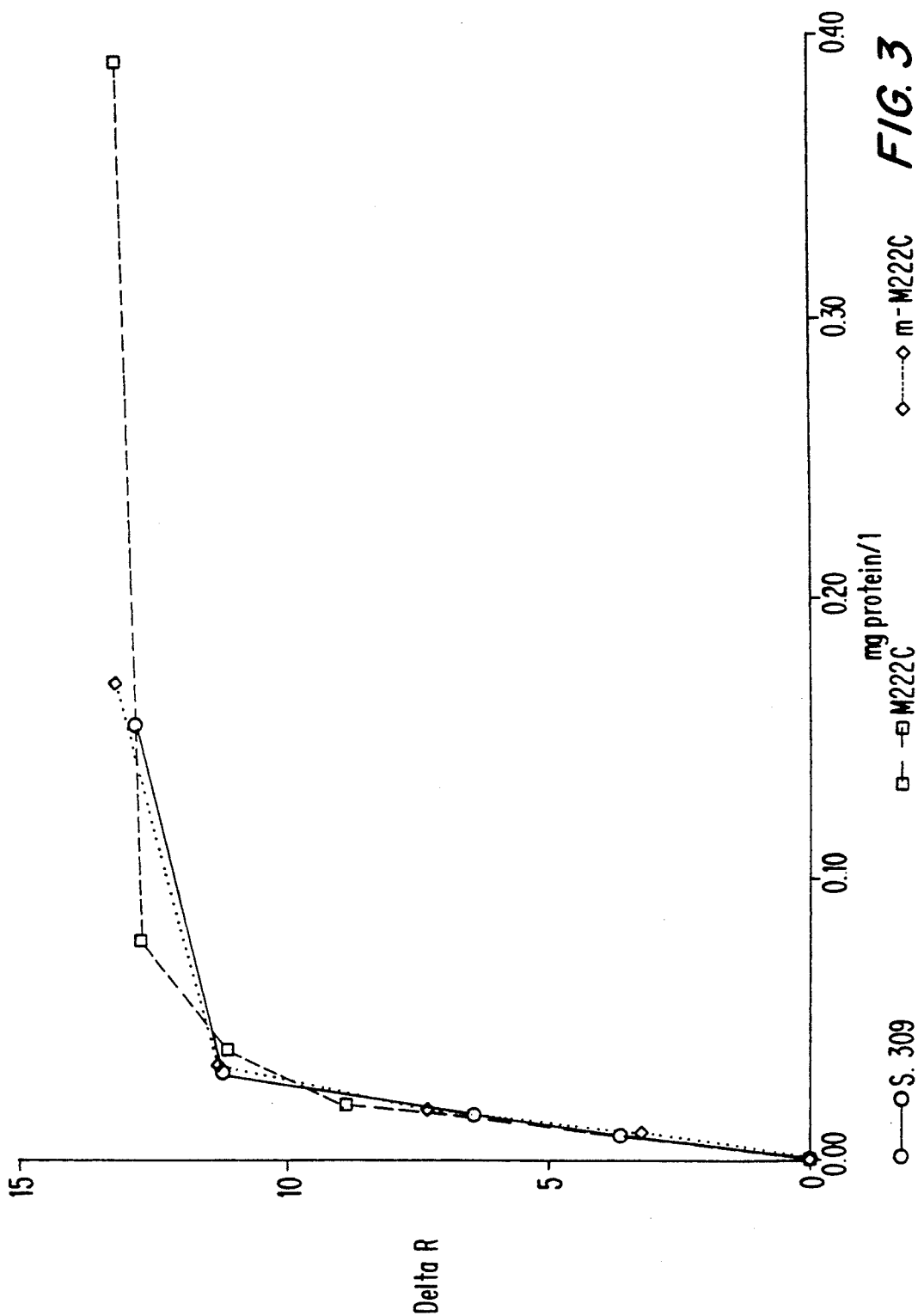
FIGS. 3 to 5 show the relation between wash performance and enzyme concentration in different detergent compositions for the wild type enzyme, the methionine substituted enzyme, and one chemically modified enzyme according to this invention.
Figure 4:
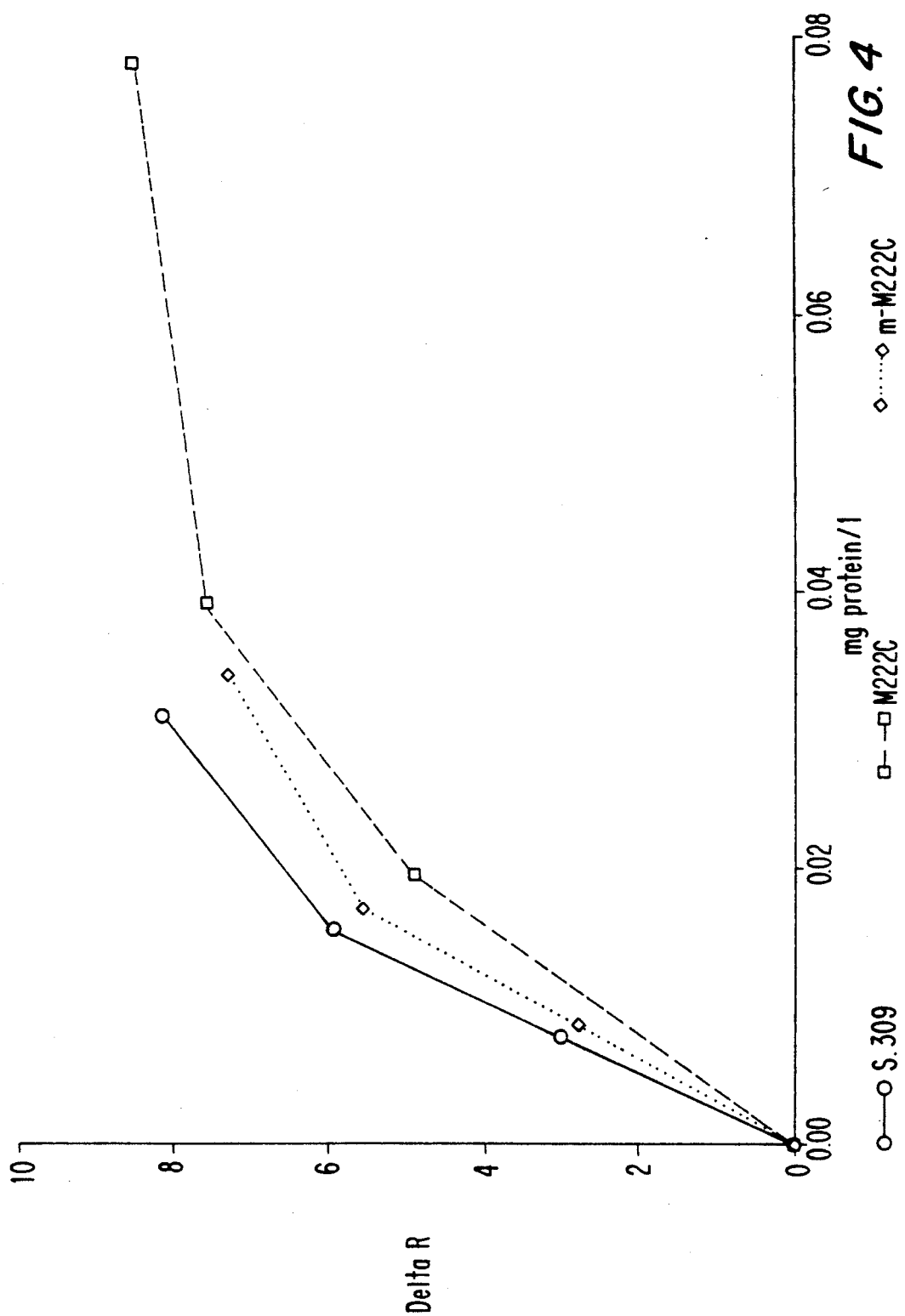
Figure 5:
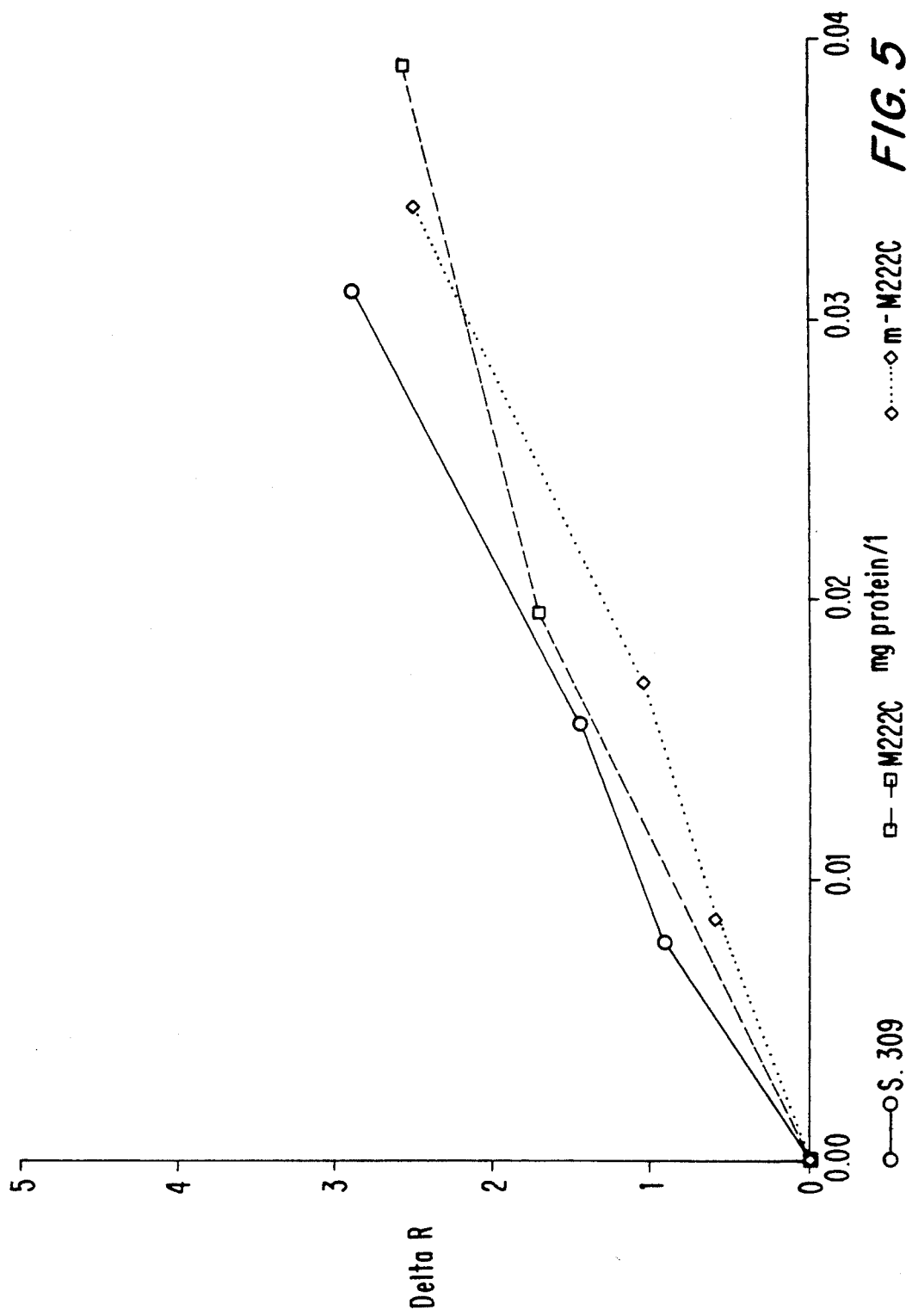

The additive of the invention can be formulated e.g. as dust free granulates, liquids, slurries, etc. Preferred detergent additive formulations are non-dusting granulates or stabilized liquids. Dust free granulates may be produced e.g. according to GB 1,362,365 or U.S. Pat. No. 4,106,991. The detergent enzymes may be mixed before or after granulation. In the case of a liquid additive, enzyme stabilizing agents may be included, or the enzymes may be protected according to EP 238,216. From studies in wash performance it is demonstrated that chemically modified subtilisin variants according to the present invention possess washability in magnitude of that of the "wild-type" subtilisin and the non-modified M222C-variant. The wash performance is tested in examples 3 to 5, and the results are set up in FIGS. 3 to 5.

Due to a novel chemical modification process according to the present invention it is therefore possible to obtain novel subtilisin variants. These novel chemically modified subtilisin variants according to the present invention possess excellent stability towards oxidative agents as well as a relatively high enzymatic activity. Moreover, their wash performance is retained in comparison to their parent enzymes.

Materials and methods

Modifying chemical reagents of the general formula $R^1SSO_2R^2$ are commercially available, or can be prepared by traditional organic chemical methods from a common precursor, sodium methanethiolsulphonate, obtained by reaction of methane sulfonyl chloride and sodium sulphide, as described by Shaked et al.; Biochemistry; 19, 4156–4166 (1980). MMTS, EMTS and PMTS e.g. are then synthezised by reaction of sodium methanethiolsulphonate with bromomethane, bromoethane and bromopropane, respectively.

The extent of the modifying chemical reaction can be monitored by e.g. Ellman's reaction, applied on the modified subtilisin variant. This reaction is carried out as described in the example.

The proteolytic activity can be monitored spectrophotometrically at 25° C., following the degradation of the peptide substrates Suc-Ala-Ala-Pro-Phe-pNA (Suc=Succinyl and pNA=p-nitro-anilid) or DMC (dimethyl-casein), and subsequent calculation of the kinetic parameters $k_{cat}$ and $K_M$.

The proteolytic activity can also be determined by the dimethyl-casein (DMC) method, described in publication AF 101/4-gb (or later editions), available on request to NOVO NORDISK A/S, Denmark, which publication is hereby included by reference.

$t_{178}$ is the half life of the enzyme, and is measured in 0.1 M $H_2O_2$, pH 6.5 at approximately 25° C. by the decrease of proteolytic activity.

The wash performance tests were accomplished on grass juice soiled cotton, prepared in the following way:

Test cloths (2.2 cm×2.2 cm, approx. 0.1 g) were produced by passing desized cotton (100% cotton, DS 71) cloth through the vessel in a Mathis Washing and Drying Unit, type TH (Werner Mathis AG, Zurich, Switzerland) containing grass juice. Finally the cloth was dried in a strong air stream at room temperature, stored at room temperature for 3 weeks, and subsequently kept at −18° C. prior to use.

Subsequent to washing, the cloths were flushed in running tap-water for 25 minutes in a bucket. The cloths were then air-dried overnight (protected against daylight), and the remission, R, was determined on an EL-REPHO 2000 photometer from Datacolor S.A., Dietkikon, Switzerland, at 460 nm.

As a measure of the wash performance differential remission, delta R, was used being equal to the remission after wash with enzyme added, minus the remission after wash with no enzyme added.

The following examples will further illustrate the present invention. The examples demonstrating certain specific embodiments of the invention should not be interpreted as limiting for the scope of this invention which should be defined by the appended claims in conjunction with this specification and examples.

EXAMPLE 1

Chemical-Modification of Subtilisin-309-M222C-Variant

Subtilisin-309-M222C variant was produced as indicated in International Patent Publication No. WO 89/06279, which is hereby incorporated by reference, and kept in a buffer solution consisting incorporated by reference, and kept in a buffer solution consisting of 10 mM MES (2-[N-morpholino]ethanesulphonic acid), 200 mM boric acid, 2 mM $CaCl_2$, <0.1 M NaCl, with pH 6.5. The enzyme was desalted on a P4 gel filtrating column (from Bio Rad), equilibrated with 5 mM MES and 2 mM $CaCl_2$ at pH 6.5.

The modification was carried out by adding to 6.2 ml M222C, $Abs_{280}=9.7$, 0.55 ml 1 M CHES (2-[N-cyclohexylamino]-ethanesulphonic acid), pH 9.5 (from SIGMA) and 0.25 ml 943 mM methane-methyl-thiosulphonate (MMTS) (from Aldrich-Chemie) in ethanol. This mixture was left at room temperature for 60 min. The mixture was then desalted on a 48 ml P4 column, equilibrated with 5 mM MES and 2 mM $CaCl_2$, with pH 6.5. Fractions from the column with highest absorbance were pooled, 10 ml, $Abs_{280}=5.79$, 95% yield.

To ensure that the cysteines had reacted, Ellman's reaction was carried out on the modified enzyme. During this reaction, Ellman's reagent, 2.2-dinitro-5.5-dithiodibenzoic acid, reacts with the free SH-group, and a nitro-mercapto-benzoic acid is released. This liberation can be monitored at 412 nm, where $\Delta\epsilon=13600$ $M^{-1}Cm^{-1}$.

The enzyme was denatured by making the solution 0.1 M in respect to HCl, followed by freeze drying and dissolution in a buffer solution, consisting of 50 mM Bicine (N,N-bis[2-hydroxyethyl]-glycine), 2 mM $CaCl_2$ and 0.1 M KCl, with pH 8.5. 900 μl of this solution were pipetted into a cuvette, and 900 μl of the buffer solution were used as a reference. $Abs_{280}$ was used to measure the concentration of enzyme. 10 μl of 10 mM Ellman's reagent in methanol were added to both cuvettes. The change in absorbance at 412 nm relates to the number of free SH-groups. In the reaction product, subtilisin-309-M222C-SM, no free SH-groups exist, meaning that the introduced cysteines in subtilisin-309-M222C had become modified. In subtilisin-309-M2220C, used as a reference, the introduced cysteines was recovered due to reaction of the free SH-group with Ellman's reagent (90%). This demonstrates that cysteines had become modified in the reaction product subtilisin-309-M222C-SM.

As a further control, the enzyme was titrated with phenyl-Hg-Cl. When subtilisin-309-M222C is modified with phenyl-Hg-Cl, the activity decreases. When the ratio phenyl-Hg-Cl/WT exceeds 1, the activity constantly remains 10% of the activity of the non-modified enzyme, corresponding to 1 group per enzyme being modified. In a similar reaction of the product subtilisin-309-M222C-SM with phenyl-Hg-Cl, no activity change is observed, even in the case of an excess of phenyl-Hg-Cl relative to subtilisin-309-M222C-SM of 2.5. This demonstrates that the free cysteines in subtilisin-309-M222C has become modified in the product subtilisin-M222C-SM.

EXAMPLE 2

Comparative characterisation

For kinetic characterization, the savinase enzymes were assayed in:

50 μl enzymatic solution
900 μl 50 mM Bicine, 2 mM CaCl₂, 0.1 M KCl, pH 8.5
50 μl X mM Suc-Ala-Ala-Pro-Phe-pNA in DMF wherein the cleavage of substrate between Phe and pNA (p-nitro-anilid) is monitored spectrophotometrically at 410 nm, $\Delta\epsilon = 8500 M^{-1} cm^{-1}$. The enzymatic concentrations are determined from the absorption at 280 nm, using $\Delta\epsilon_{28}$ determined from the amino acid composition, $\Delta\epsilon_{280} = 23217 M^{-1} cm^{-1}$.

The kinetic parameters $k_{cat}$ and $K_M$ are determined from a direct fit of the initial velocities at 7 concentrations of substrate to the Michaelis Menten equation. The enzyme concentration, X, is varied from 4 to 131 mM, so that the concentration of the substrate in assay varies from 0.2 to 6.5 mM. Thus selected around the $K_M$ value of the enzymes.

The lapse of time for the effect of 0.1 M $H_2O_2$ on the activity of the wild type and mutant enzymes is investigated by incubating the enzymes, approx. 0.5 μM, in 5 mM MES, 2 mM CaCl₂, pH 6.5, with $H_2O_2$ (from a 30% stock solution, MERCK). At regular interval times the reaction was stopped by diluting an appropriate amount of enzyme in assay with 0.35 mM Suc-Ala-Ala-Pro-Phe-pNA, 50 mM Bicine, 2 mM CaCl₂, 0.1 M KCl, pH 8.5, and monitoring the change in absorbance at 410 nm. The remaining activity is determined as the percentage of activity on non-treated enzyme control. The half-life, $t_{\frac{1}{2}}$, corresponding to 50% of activity remaining, is determined from the activity curves.

The characterisation results are set up in table 2 shown previously.

Wash Performance Test

EXAMPLE 3

Wash performance A 5.0 g/l of a commercial European type powder detergent (A) with perborate and activator were used. The detergent was dissolved in approx. 9° dH (German Hardness) water, and pH was measured to 10.2. The test was performed in a Terg-o-tometer test washing machine (described in Jay C. Harris; Detergency, Evaluation and Testing; Interscience Publishers Ltd. (1954), p. 60–61) at 40° C., isothermically for 10 minutes at 100 rpm.

The modified subtilisin-309-M222C-SM variant was compared to the wild type enzyme and the non-modified subtilisin-309-M222C variant.

The enzymes were dosed from 0.008 to 0.4 mg protein/l. From the results in FIG. 3 it appears that the 3 enzymes perform equally well on a protein basis.

EXAMPLE 4

Wash performance B 5.0 g/l of a commercial European type powder detergent (B) with perborate and activator were used. The detergent was dissolved in approx. 9° dH water, and pH was measured to 9.5. The test was performed in a Terg-o-tometer at 40° C., isothermically for 10 minutes at 100 rpm.

The modified subtilisin-309-M222C-SM variant was compared to the wild type enzyme and the non-modified subtilisin-309-M222C variant.

The enzymes were dosed from 0.008 to 0.08 mg protein/l. From the results in FIG. 4 it appears that the 3 enzymes perform equally well on a protein basis.

EXAMPLE 5

Wash performance C 1.1 g/l of a commercial US type powder detergent (C) with perborate and activator were used. The detergent was dissolved in approx. 6° dH water, and pH was measured to 9.5. The test was performed in a Terg-o-tometer at 40° C., isothermically for 10 minutes at 100 rpm.

The modified subtilisin-309-M222C-SM variant was compared to the wild type enzyme and the non-modified subtilisin-309-M222C variant.

The enzymes were dosed from 0.008 to 0.08 mg protein/l. From the results in FIG. 5 it appears that the 3 enzymes perform equally well on a protein basis.

We claim:

1. A modified enzyme, wherein one or more methionine residues of a detergent enzyme are replaced by cysteine having an HS-group, wherein said cysteine residue(s) are further modified by replacing the hydrogen atom of the HS-group with a group of formula $R^1S-$, wherein $R^1$ is $C_{1-6}$-alkyl.

2. The modified enzyme according to claim 1, wherein the detergent enzyme is selected from the group consisting of an amylase, lipase, cellulase and protease.

3. The modified enzyme according to claim 2, wherein the detergent enzyme is a subtilisin.

4. The modified enzyme according to any of claims 1–3, wherein $R^1$ is $C_{1-3}$-alkyl.

5. A modified enzyme, wherein a subtilisin is modified by replacing the methionine residue in position 222 with cysteine having an HS-group, wherein the cysteine residue is further modified by replacing the hydrogen atom of the HS-group with a group of the formula $R^1S-$, wherein $R^1$ is $C_{1-6}$-alkyl.

6. The modified enzyme according to claim 5, wherein the subtilisin is selected from the group consisting of subtilisin-309, subtilisin-147, subtilisin BPN', subtilisin Carlsberg and proteinase K.

7. The modified enzyme according to claim 6, wherein the subtilisin is subtilisin-309.

8. The modified enzyme according to any of claims 5–7, wherein $R^1$ is $C_{1-3}$-alkyl.

9. The modified enzyme according to claim 8, wherein $R^1$ is methyl.

10. The modified enzyme according to claim 8, wherein $R^1$ is propyl.

11. A detergent composition comprising a modified enzyme according to claim 1 and a surfactant.

12. A detergent additive comprising a mutant enzyme according to claim 1 which is in the form of a non-dusting granulate or a stabilized liquid.

* * * * *